(12) United States Patent
Ikuta

(10) Patent No.: US 11,941,784 B1
(45) Date of Patent: Mar. 26, 2024

(54) IMAGE PROCESSING APPARATUS, METHOD, AND STORAGE MEDIUM FOR SPECTRALLY ENCODED ENDOSCOPY GHOST NOISE REDUCTON

(71) Applicant: Canon USA, Inc., Melville, NY (US)

(72) Inventor: Mitsuhiro Ikuta, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 335 days.

(21) Appl. No.: 17/198,077

(22) Filed: Mar. 10, 2021

Related U.S. Application Data

(60) Provisional application No. 63/016,110, filed on Apr. 27, 2020.

(51) Int. Cl.
*G06T 5/00* (2006.01)
*A61B 1/00* (2006.01)
*G06N 20/00* (2019.01)
*G06T 5/20* (2006.01)

(52) U.S. Cl.
CPC ........ *G06T 5/002* (2013.01); *A61B 1/000095* (2022.02); *G06N 20/00* (2019.01); *G06T 5/20* (2013.01); *G06T 2207/10068* (2013.01); *G06T 2207/20081* (2013.01); *G06T 2207/20132* (2013.01); *G06T 2207/20182* (2013.01)

(58) Field of Classification Search
None
See application file for complete search history.

(56) References Cited

U.S. PATENT DOCUMENTS

| | | | | |
|---|---|---|---|---|
| 11,073,695 | B2* | 7/2021 | Gao | H04N 13/383 |
| 2003/0210047 | A1* | 11/2003 | Mitchell | G01R 33/56 |
| | | | | 324/309 |
| 2010/0182452 | A1* | 7/2010 | Utsugi | H04N 23/80 |
| | | | | 348/241 |
| 2010/0228129 | A1* | 9/2010 | Osumi | A61B 8/4483 |
| | | | | 600/443 |
| 2011/0188705 | A1* | 8/2011 | Tabaru | G06V 10/431 |
| | | | | 382/103 |
| 2011/0249151 | A1* | 10/2011 | Ito | G06T 5/002 |
| | | | | 348/241 |
| 2018/0275333 | A1* | 9/2018 | Ishii | G02B 6/0031 |
| 2019/0362477 | A1* | 11/2019 | Rahmati | G06T 7/337 |
| 2020/0226721 | A1* | 7/2020 | Kishimoto | G01S 7/52077 |
| 2022/0404342 | A1* | 12/2022 | Ding | G01N 33/54366 |
| 2023/0048725 | A1* | 2/2023 | Barbour | G06T 7/0012 |

* cited by examiner

*Primary Examiner* — Randolph I Chu
(74) *Attorney, Agent, or Firm* — Canon U.S.A., Inc. IP Division

(57) ABSTRACT

An image processing apparatus includes at least one memory and at least one processor that executes instructions stored in the memory to receive an input image based on image data, execute noise reduction processing on the image data, and output noise-reduced output data based on a result of the noise reduction processing, wherein the noise reduction processing calculates a value using reference pixels based on a first frequency range, and subtracts a value using pixels based on a second frequency range.

17 Claims, 10 Drawing Sheets

IMAGE PROCESSING APPARATUS, METHOD, AND STORAGE MEDIUM FOR SPECTRALLY ENCODED ENDOSCOPY GHOST NOISE REDUCTON

CROSS REFERENCE TO RELATED APPLICATIONS

The present application claims the benefit of priority from U.S. Provisional Patent Application No. 63/016,110 filed Apr. 27, 2020, which is hereby incorporated by reference herein in its entirety.

BACKGROUND

Field of the Disclosure

The present disclosure generally relates to image processing and, more particularly, to an image processing apparatus, an image processing method, and a storage medium for spectrally encoded endoscopy (SEE) ghost noise reduction.

Description of the Related Art

Illumination light diffracted in a lower order than an imaging order can partially go to an imaging target, and may be collected by detection optics. That may cause noise in imaging (ghost noise).

Ghost noise detrimentally affects imagery that may take place, for example, where an image sensor captures an optical image that may pass through imaging optics and be reflected between lenses or other components of the imaging optics before finally reaching the image sensor. For example, an optical image that reaches a light-receiving area of an image sensor may be converted into an electrical image signal. However, part of the optical image may be reflected at the light-receiving area, and the reflected optical image may be reflected by the lens of the imaging optics to the image sensor. The image sensor may capture both the direct optical image as well as the reflected optical image. A ghost image or noise may be generated by the reflected optical image.

It would be beneficial to overcome these concerns and provide an ability to alleviate effects of ghost noise on images of imaging targets.

SUMMARY

According to an aspect of the present disclosure, an image processing apparatus includes at least one memory and at least one processor that executes instructions stored in the memory to receive an input image based on image data, execute noise reduction processing on the image data, and output noise-reduced output data based on a result of the noise reduction processing, wherein the noise reduction processing calculates a value using reference pixels based on a first frequency range, and subtracts a value using pixels based on a second frequency range.

Further features of the present disclosure will become apparent from the following description of exemplary embodiments with reference to the attached drawings.

DESCRIPTION OF THE EMBODIMENTS

Various exemplary embodiments, features, and aspects of the disclosure will be described below with reference to the drawings.

In the present disclosure, configurations are described that may functionally implement intravascular imaging modalities including, for example, spectrally encoded endoscopy (SEE), optical coherence tomography (OCT), intravascular ultrasound (IVUS), combinations or hybrids thereof, or the like. The present disclosure is not limited to any particular configuration.

Figure 1:
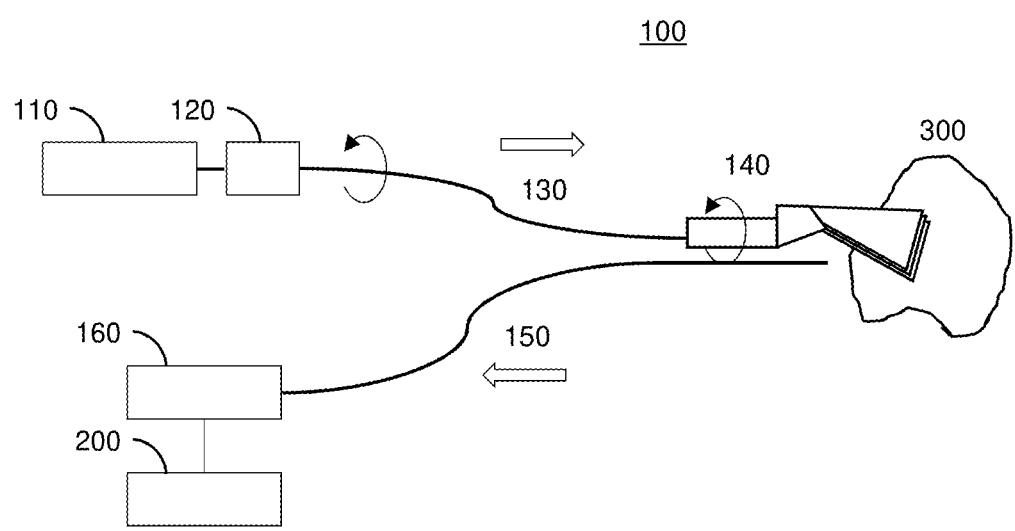
FIG. 1 illustrates an image processing apparatus according to an exemplary aspect of the present disclosure.

FIG. 1 is an illustration of an image processing apparatus configured as an SEE apparatus 100 according to one or more aspects of the present disclosure. The SEE apparatus 100 can encode spatial information on a sample 300 based on wavelengths. Depth and distance characteristics of a sample can be obtained through use of phase of the reflected light. A grating at a tip of imaging optics diffracts broadband light into multiple beams, where each beam can be illuminated on a transverse location of a sample. Each beam may differ from other beams, and each location may differ from other locations. The SEE apparatus 100 facilitates acquisition of high-definition images.

The SEE apparatus 100 may include, for example, one or more of a light source 110, a rotary junction 120, an illumination fiber 130, a probe 140, a detection fiber 150, a spectrometer 160, a controller 200, and can include other elements. The light source 110 emits light in the form of broadband light or other electro-magnetic illumination. The light may be coupled into a light guiding component which can be the illumination fiber 130.

The light source 110 is broadband light with a bandwidth enabling spatial resolution along a spectrally dispersed dimension, and may include a plurality of light sources or may be a single light source. The light source 110 includes, for example, one or more of a laser, a light emitting diode (LED), an organic LED (OLED), a halogen light, an incandescent light, a fluorescent light, or the like. The light source 110 can be fiber coupled or free space coupled to another component of the SEE apparatus 100. The light source 110 provides light which is split up into at least three bands in which each band can be further dispersed to provide light which is then used for spectral encoding of spatial information.

The light source 110 disperses light or is incident on a sample 300 at various wavelengths. The light is within an imaging spectrum bandwidth that can be a mixture of various wavelengths in a wavelength range including, for example, infrared, ultraviolet, other ranges, and can include the entire visible spectrum. Wavelength categories, for example, can be 250-1000 nm that generally includes ultraviolet, visible, and near infrared light, 1000-3000 nm that generally includes mid-wave light, and 3000-18000 nm that generally includes thermal infrared light.

The light source 110 has broadband visible light sources that include a band of light including wavelengths $\lambda_1$ to $\lambda_N$.

Broadband visible light sources include one or more of a blue band of light including wavelengths $\lambda_{B1}$ to $\lambda_{BN}$, a green band of light including wavelengths $\lambda_{G1}$ to $\lambda_{GN}$, a red band of light including wavelengths $\lambda_{R1}$ to $\lambda_{RN}$, or the like. For example, the blue band can contain 400-500 nm light, the green band can contain 500-600 nm light, and the red band can contain 600-800 nm light.

The wavelengths of the broadband light can be optimized for identifying specific features including, for example, blood, tissue, or the like, and can extend into the near infrared region, for example 1200 nm. Each wavelength band can have a wavelength range that is greater than 30 nm.

The light source 110 can include at least three bands to facilitate and produce color images. More bands may be used as desired to acquire additional information.

The illumination fiber 130 is a light guiding component or other optical waveguide which is connected to the probe 140. The illumination fiber 130 is a single-mode fiber, a multi-mode fiber, or a double clad fiber. Preferably, a single-mode fiber is used as the illumination fiber 130. The probe 140 or parts thereof can be rotated or oscillated as indicated by the arrow. For example, the illumination fiber 130 and illumination optics can be rotated via a motor, such as a Galvano motor or the like.

The rotary junction 120 is configured to rotate the probe 140, and includes a motor that is removably coupled to the proximal portion of the probe 140. The rotary junction 120 can be a fiber optic rotary joint (FORJ) or the like, and can have one or more of a stationary section and a rotatable section. The motor has a shaft that can be hollow to allow a portion of the rotatable section of the FORJ to extend therethrough. In a power-on or active state where the motor is activated, the rotatable section of the FORJ rotates, thereby causing a driveshaft and the illumination fiber 130 and other rotatable section(s) to rotate.

The FORJ allows an optical signal to be transmitted across an interface between the rotatable section and the stationary section. The FORJ uses optical signals to carry high speed digital data, or analog data with frequency or amplitude sensitive, e.g. analog information. The FORJ can be single or multi-pass and passive or active. A passive FORJ transmits an optical signal from a rotating structure to a stationary structure without any electronic processing although components such as filters and lenses can be used to process the optical signal. An active FORJ incorporates electronics to process a signal to improve rotor to stator transmission properties and implements one or more of electrical/optical conversion, amplification, signal conditioning and re-clocking.

The motor is rotationally linked through a belt to the junction or FORJ, which connects the probe 140 via a connector to translate rotational torque. The junction can have an optic rotary joint and a brushed electrical slip ring for OCT signal coupling to allow the whole probe 140 to rotate freely. These components are fixed to a linear translation stage which function for imaging pullback.

The illumination fiber 130 transmits broadband light to the probe 140. The detection fiber 150 is a second light guiding component that collects light from the sample 300.

The probe 140 includes one or more elongated or tubular members including, for example, an inner sheath and an outer sheath. The illumination fiber 130 can be disposed within the inner sheath. The detection fiber 150 can be arranged within the outer sheath and the outer sheath can be disposed around the inner sheath. The illumination fiber 130 and the detection fiber 150 can be driven by one or more different motors. The probe 140 includes a lens, for example, a gradient index (GRIN) lens, a ball lens, a spherical lens, an aspherical lens, combinations thereof, or the like. The probe 140 is configured as a forward-viewing or side-viewing probe. In a side-viewing probe, the incident light can be bent with respect to an optical axis of the probe 140.

The probe 140 includes one or more windows at the distal end of the fibers or waveguide(s). The inner surface or outer surface of the window(s) can be coated with an optical coating that alters the way in which the window(s) transmit and reflect light. The optical coating reflects wavelengths and creates reference markers on imaging data to reveal accurate position information regarding distances between the detection fiber(s) and the reflecting surface of the window at a particular rotation angle. The position information can be correlated to a particular scan to form an undistorted image of a scanned surface.

The illumination fiber 130 and the detection fiber 150 can be configured as an optical fiber or similar waveguide, circular, rectangular, or the like, and can include polymer, glass, silicon, air, or combinations thereof. The light source 110 is coupled to the illumination fiber 130. The probe 140 can be disposable and can include a tube with an electrode. The tube can be a flexible tube of material such as PTFE (polytetrafluoroethylene), Teflon, or the like, and the electrode can be a tungsten electrode.

The illumination fiber 130 and the detection fiber 150 can be single-mode or multimode optical fibers, photonic crystal fibers, photonic bandgap fibers, polarization maintaining fibers, or the like, and can include one or more fibers, a plurality of fibers, a fiber bundle, or the like. Single-mode optical fibers support a single optical mode, and multimode optical fibers support multiple optical modes.

The illumination fiber 130 and the detection fiber 150 can be configured as fiber optic cables that include a few optical fiber threads or several hundred optical fiber threads, each of which can transmit data modulated into light waves. The optical fibers can include a transparent core having a higher index of refraction surrounded by a transparent cladding material with a lower index of refraction. Light is kept in the core by a phenomenon of total internal reflection, and some light can travel in cladding as an evanescent wave, which includes all the wavelengths of the light that are outputted by the light source 110.

The spectrometer 160 measures light reflected from the sample 300 that has been illuminated by the light source 110 having known parameters or characteristics, where each resolvable wavelength may correspond to a different point on the sample 300. The spectral output data has values representing a spectral power distribution of the detected light. The spectral output data can be compared to light from the light source 110. The spectrometer facilitates analysis and visualization of spectrally encoded information.

Figure 2:
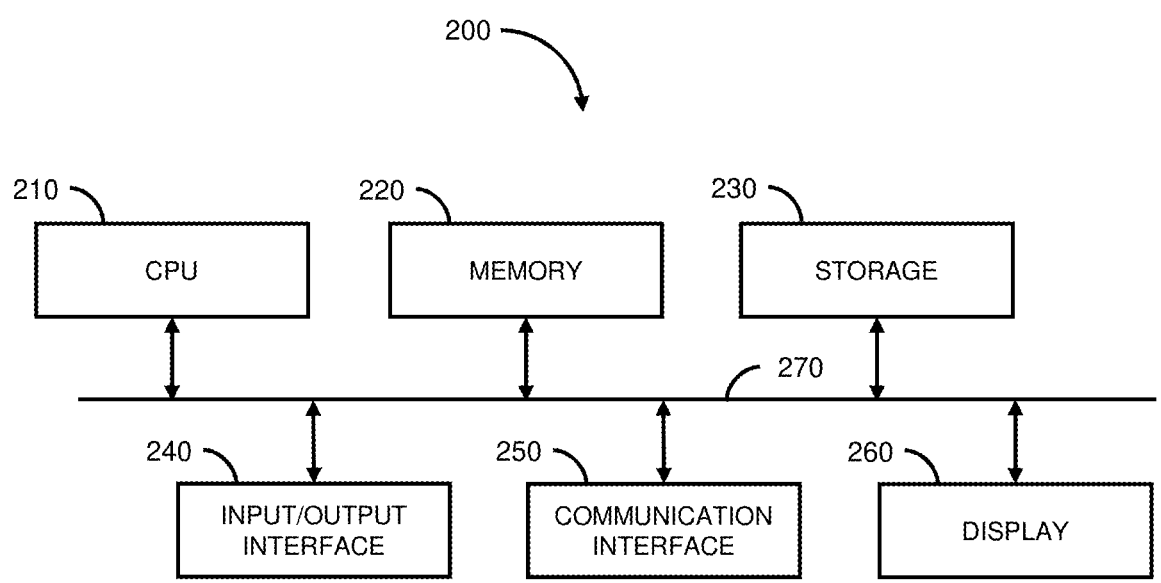
FIG. 2 illustrates a controller according to an exemplary aspect of the present disclosure.

FIG. 2 illustrates the controller 200 according to one or more aspects of the present disclosure. The controller 200 is configured to control the elements of the SEE apparatus 100 and may include one or more configurational components including, for example, a CPU 210, a memory 220, a storage 230, an input and output (I/O) interface 240, a communication interface 250, a display 260, and can include other elements. The CPU 210 includes one or more processors, circuitry, or a combination thereof, and is configured as a control circuit or circuitry for performing overall control of the SEE apparatus 100 and components connected to the SEE apparatus 100. The SEE apparatus 100 can be interconnected with medical instruments or other devices, and can be controlled independently, externally, or remotely by the controller 200.

The memory 220 is used as a work memory. The storage 230 stores software or computer instructions, and can save various types of data such as SEE images, other image configurations, or the like. The storage 230 may be configured as a hard disk drive (HDD), a solid-state drive (SSD), or the like. The CPU 210 executes the software developed in the memory 220 to execute the processing of the SEE apparatus 100 and components connected to the SEE apparatus 100, and various parameters for use in image processing. The I/O interface 230 inputs information from the SEE apparatus 100 to the controller 200 and outputs information for displaying to the display 260.

The communication interface 250 may be configured as a circuit or other device for communicating with components included the apparatus 100, and with various external apparatuses connected to the apparatus via a network. For example, the communication interface 250 may store information to be output in a transfer packet and output the transfer packet to an external apparatus via the network by communication technology such as Transmission Control Protocol/Internet Protocol (TCP/IP). The apparatus may include a plurality of communication circuits according to a desired communication form.

The controller 200 can be communicatively interconnected or interfaced with one or more external devices including, for example, one or more data storages, one or more external user input/output devices, or the like. The controller 200 can interface with other elements including, for example, one or more of an external storage, a keyboard, a mouse, a sensor, a microphone, a speaker, a projector, a scanner, an illumination device, or the like.

The display 260 is a display device configured, for example, as a monitor, an LCD (liquid panel display), an LED display, an OLED (organic LED) display, a plasma display, an organic electro luminescence panel, or the like. Based on the control of the apparatus 100, a screen may be displayed on the display 260 showing one or more images being captured, captured images, captured moving images recorded, data or other information on the storage 230, or the like.

The components are connected together by a bus 270 so that the components can communicate with each other. The bus 270 transmits and receives data between these pieces of hardware connected together, or transmits a command from the CPU 210 to the other pieces of hardware. The components can be implemented by one or more physical devices that may be coupled to the CPU 210 through a communication channel. For example, the controller 200 can be implemented using circuitry in the form of ASIC (application specific integrated circuits) or the like. Alternatively, the controller 200 can be implemented as a combination of hardware and software, where the software is loaded into a processor from a memory or over a network connection. Functionality of the controller 200 can be stored on a storage medium, which may include RAM (random-access memory), ROM (read only memory), magnetic or optical drive, diskette, cloud storage, or the like.

The units described throughout the present disclosure are exemplary and/or preferable modules for implementing processes described in the present disclosure. The term "unit", as used herein, may generally refer to firmware, software, hardware, or other component, such as circuitry or the like, or any combination thereof, that is used to effectuate a purpose. The modules can be hardware units (such as circuitry, firmware, a field programmable gate array, a digital signal processor, an application specific integrated circuit or the like) and/or software modules (such as a computer readable program or the like). The modules for implementing the various steps are not described exhaustively above. However, where there is a step of performing a certain process, there may be a corresponding functional module or unit (implemented by hardware and/or software) for implementing the same process. Technical solutions by all combinations of steps described and units corresponding to these steps are included in the present disclosure.

Figure 3:
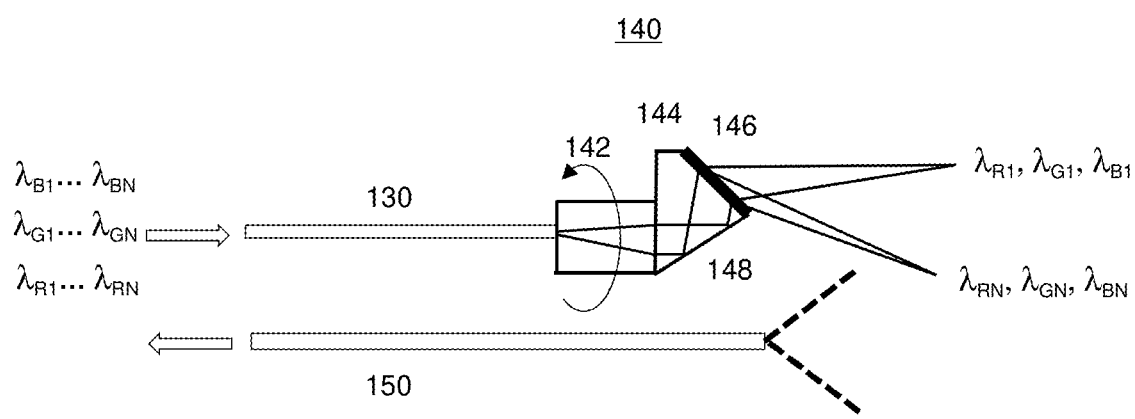
FIG. 3 illustrates a probe schematic according to an exemplary aspect of the present disclosure.

FIG. 3 is an illustration of a portion of the SEE apparatus 100 showing a schematic of the probe 140 according to one or more aspects of the present disclosure.

For example, the shortest wavelength light in each color bandwidth, ($\lambda_{R1}, \lambda_{G1}, \lambda_{B1}$), may be diffracted to the sample 300 in a forward-view direction.

The light guiding component or illumination fiber 130 may transmit broadband light to the probe 140. A second light guiding component or detection fiber 150 may collect light from the sample 300. The probe 140 may include a light focusing component 142 and a grating component 146 which may be attached to a spacer 144.

The grating component 146 may include one or more reflecting elements that may be used in connection with other elements to move the light, incrementally, progressively, discontinuously, or the like, and may use light redirecting devices including refracting or diffracting elements for one or more narrow or planar beams of light. These may include, for example, mirrors, prisms, electric lenses, acousto-optic deflectors, spatial light modulators, beam steering mirrors or optics, flexible optical light guides or fibers, or the like, to control the directions of outgoing and incoming light.

The grating component 146 may be a diffraction grating with a periodic structure, and may include grooves that are spaced a distance apart. The periodic structure may split and diffract light into several beams travelling in different directions. A light ray having a wavelength may be incident at an angle and may be diffracted by a grating of a groove spacing along a number of angles. The relationship among the angles and the groove distance may be described by refractive indices of the material where the ray is incident and diffracted, and may be referred to as a diffraction order, or spectral order, and may be an integer.

The portion of the light focusing component 130 where the light guiding component 130 attaches is preferably a polished end of a lens.

The second light guiding component 150 can be, for example, a GRIN lens or a ball lens and may be fixed to an angle-polished spacer 144.

The spacer 144 may configured of glass, heat-curable resin, UV-curable resin, plastic, or the like. The light guiding component 130 may be centered or off-centered from the second light guiding component 150. The second light guiding component 150 may be a light focusing component.

In a centered case the light direction exiting the second light guiding component 150 may be substantially parallel to an optical axis of the second light guiding component 150. In an off-centered case the light direction exiting the second light guiding component 150 may be at an angle relative to the optical axis of the second light guiding component 150 depending on the off-centered amount.

The grating 146 may be fabricated by techniques such as dry-etching, wet-etching, nano-imprint, soft lithography, or the like. The grating 146 may be formed directly on the spacer 144. For example, the spacer 144 with grating 146 may be fabricated by dicing and angle-polishing etched glass grating. The grating 146 may be a binary grating, a blazed grating, a holographic grating, or the like.

Figure 4:
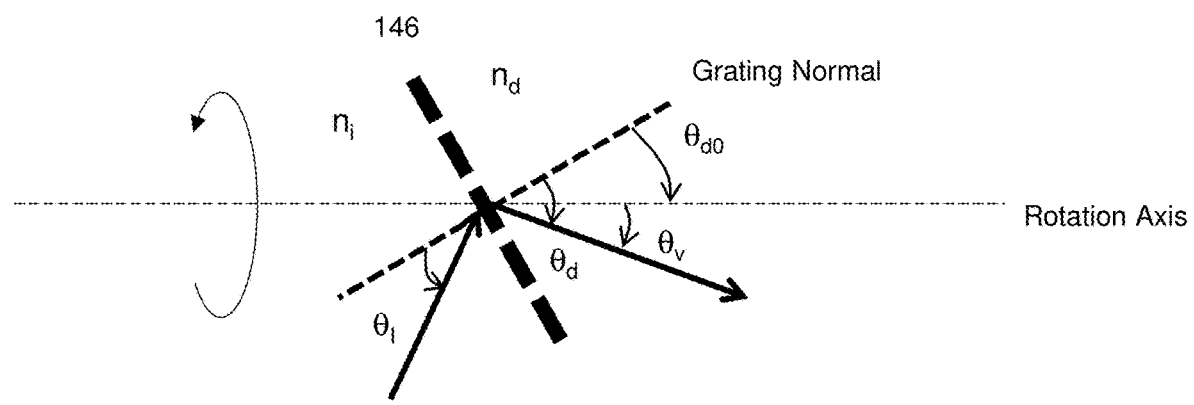
FIG. 4 illustrates a grating function according to an exemplary aspect of the present disclosure.

A function of the grating 146 is illustrated by FIG. 4. The light may be incident on the grating 146 at substantially a same incident angle $\theta_i$. A diffraction angle $\theta_d$ may be determined by a grating equation such as equation (1):

$$n_i \sin \theta_i + n_d \sin \theta_d = -mG\lambda \quad (1)$$

where $n_i$ is representative of refractive index of the material on the incident side of the grating 146; $n_d$ it is the refractive index of the material on the diffraction side of the grating; m may be an integer indicating the diffraction order; G is spatial frequency of the grating 126, and $\lambda$ is wavelength of the light.

In an exemplary embodiment, for example, the diffraction conditions may be: $n_i=1.5037$; $n_d=1$; $\theta_i=42.81°$; and G=650/mm. The grating 146 may be configured so that the absolute value of the product of the spatial frequency G and the diffraction order for green light $m_G$, $|m_G{}^G|$, may be more than 2000/mm, 2500/mm, or 3000/mm.

In order to make a blue band of illumination light, a green band of illumination light, and a red band of illumination light may overlap on the sample 300, and a diffraction order for the blue band of light $m_B$, a diffraction order for the green band of light $m_G$, and a diffraction order for the red band of light $m_R$ may be configured to satisfy equations (2):

$$|m_B|=|m_G|+1$$
$$|m_R|=|m_G|-1$$
$$\{m_R,m_G,m_B\in \mathbb{Z} | \text{sgn}(m_R)=\text{sgn}(m_G)=\text{sgn}(m_B), (m_R,m_G,m_B)\neq 0\} \quad (2)$$

where $m_G$ may, for example, be $-4$, $-5$, $-6$, or the like.

A view angle $\theta_v$, the angle between rotation axis and illumination light direction, may be represented by equation (3):

$$\theta_v = \theta_d - \theta_{d0} \quad (3)$$

where $\theta_{d0}$ is a diffraction angle when diffracted light is parallel to rotation axis of the probe.

Figure 5:
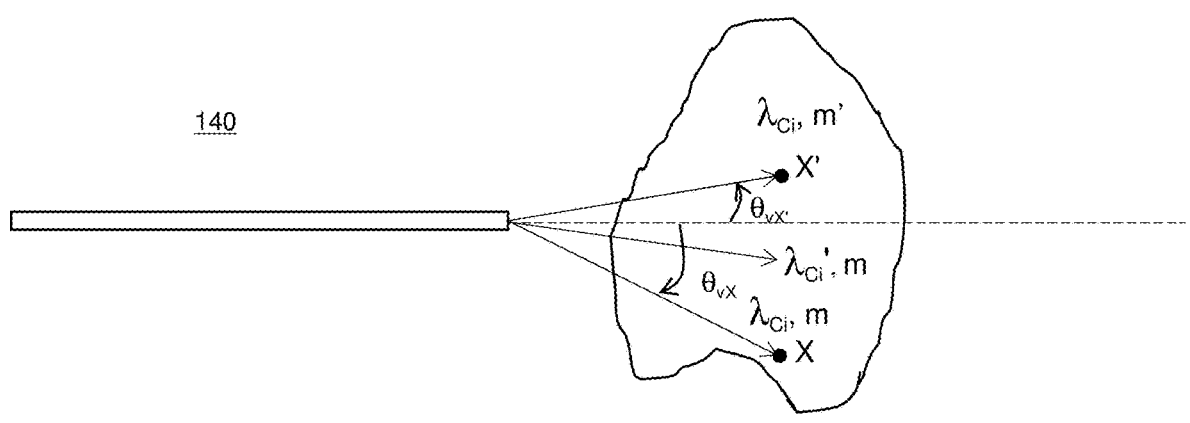
FIG. 5 illustrates ghost noise generation according to an exemplary aspect of the present disclosure.

FIG. 5 illustrates generation of ghost noise according one or more aspects of the present disclosure. A point X on the sample may be scanned when probe rotation is at certain angle by illumination light of wavelength $\lambda_{Ci}$ (C: band such as R, G, or B; i=1 to N) which may be diffracted in mth order by the probe grating, which may be configured for a diffraction order for imaging. Illumination light of the same wavelength $\lambda_{Ci}$ but diffracted in adjacent order m' may be incident on another point X' on the sample. For example, m may be a negative value equal to or less than $-1$ and m'=m+1, such as (m, m')=($-5$, $-4$).

Light of wavelength $\lambda_{Ci}$ may be reflected by sample, detected by detection optics, and may be processed to reconstruct image area corresponding to the wavelength. In the reconstructed image, images from locations X and X' may appear at the same place where image of X should appear. Image of X' may represent ghost noise image on a true image of X.

Figure 6:
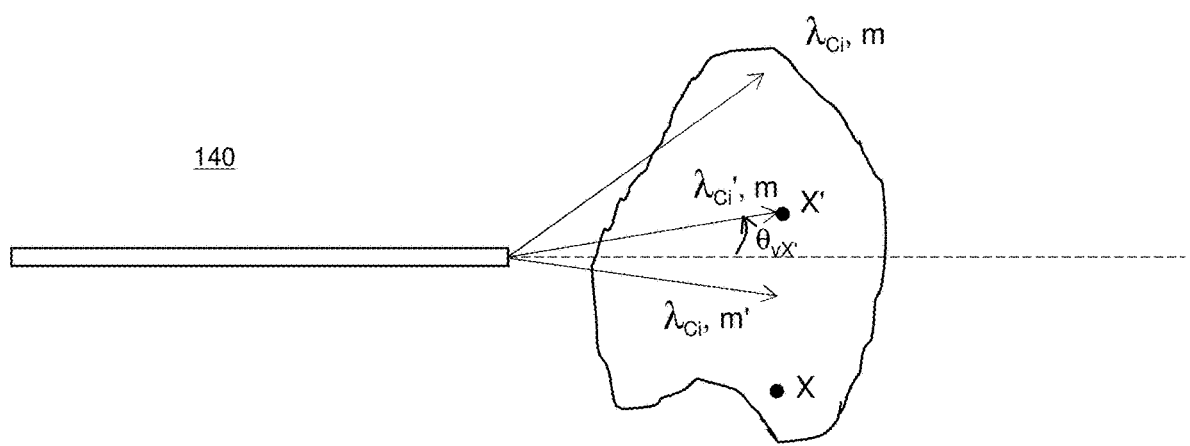
FIG. 6 illustrates the exemplary ghost noise generation of FIG. 5 rotated by 180 degrees according to an exemplary aspect of the present disclosure.

FIG. 6 shows the probe 140 when it is rotated by 180 degrees from the configuration in FIG. 5. The location X' on the sample may be illuminated by light of another wavelength/order, $\lambda_{Ci}'$ and m. Using this information, the ghost noise due to light of wavelength $\lambda_{Ci}$ and order m' in image reconstruction process may occur as exemplified in the following.

In a case where no ghost effect occurs, reflectance from a sample to a probe, $R(\theta_v, \phi, \lambda)$, may be represented by equation (4):

$$\frac{D(\lambda,t)}{ref(\lambda)} = A \cdot R(\theta_V, \varphi, \lambda) \quad (4)$$

$\lambda$ may be a wavelength, $\theta_v$ may be a view angle, $\phi$ may be a probe rotation angle, A may be a proportionality constant, $D(\lambda,t)$ may be a measured value at the spectrometer 160 at wavelength $\lambda$ and time t, and ref($\lambda$) may be a reference spectrum to normalize the value in terms of white balance. Here time t may correspond to view angle $\phi$. For example, $\phi$ may be linear function of t when probe rotation speed is uniform.

In a case where there is ghost noise in FIG. 4, the equation may be represented as equation (5):

$$\frac{D(\lambda,t)}{ref(\lambda)} = A \cdot \{R(\theta_v, \varphi, \lambda) + \alpha(\lambda) \cdot R(\theta_v', \varphi, \lambda)\} \quad (5)$$

where $\alpha(\lambda)$ may be ghost/imaging ratio at a wavelength $\lambda$ which may be a ratio of optical throughput of the system between light diffracted in the order for imaging and in the order causing ghost noise. $\theta_v'$ may be a view angle where the ghost order light illuminates.

This ratio may be obtained by measuring the same target in an imaging order and a ghost order by the probe and system separately. For example, a half circle target may be used so that either imaging order light or ghost order can illuminate the target, and the ratio may be obtained by taking the ratio of the values which are obtained at different probe rotation position, such as 0 degrees and 180 degrees.

In a case where a difference in reflectance of the target is small between $\lambda$ and $\lambda'$, the equation (5) may be represented as equation (6):

$$\frac{D(\lambda,t)}{ref(\lambda)} = A \cdot \{R(\theta_v, \varphi, \lambda) + \alpha(\lambda) \cdot R(\theta_v', \varphi + \pi, \lambda')\} \quad (6)$$

$\lambda'$ may be a wavelength of light which illuminates in imaging order the same location of the sample where light of wavelength $\lambda$ illuminates in ghost order, when the probe rotates by 180 degrees.

Grating equation (1) for those parameters may be represented as equations (7):

$$n_i(\lambda)\sin \theta_i + \sin(\theta_{d0}+\theta_v) = -mG\lambda$$
$$n_i(\lambda)\sin \theta_i + \sin(\theta_{d0}+\theta_v') = -(m+1)G\lambda$$
$$n_i(\lambda')\sin \theta_i + \sin(\theta_{d0}-\theta_v') = -mG\lambda' \quad (7)$$

In a case where $\alpha(\lambda')$ is small, this equation can be approximated as equation (8):

$$\frac{D(\lambda, t)}{ref(\lambda)} = A \cdot R(\theta_v, \varphi, \lambda) + \alpha(\lambda) \cdot \frac{D(\lambda', t')}{ref(\lambda')} \quad (8)$$

where t' is a time when probe rotation angle is φ+π. For example, if probe rotation speed is uniform, equation (9) can be:

$$t' = t \pm T/2 \quad (9)$$

where T is a period of probe rotation. In connection with the discussion above and equation (7), the reflectance of the sample may be calculated with ghost noise reduction by subtracting the second term in the following equation from the first term as equation (10):

$$A \cdot R(\theta, \varphi, \lambda) = \frac{D(\lambda, t)}{ref(\lambda)} - \alpha(\lambda) \cdot \frac{D(\lambda', t')}{ref(\lambda')}. \quad (10)$$

For example, α and ref can be prepared before imaging, that is, by obtaining sample imaging data such as D(λ, t) and D (λ', t').

Particular ghost reduction processing may differ according to imaging configurations and wavelengths, and all variations are within the scope of the present disclosure. For example, ghost reduction processing may be applied to the wavelengths where α(λ) is larger than a certain value such as 0.03, 0.06, 0.1, 0.2, 0.3, or the like.

The reference spectrum ref(λ) may be line data of a SEE image obtained with a uniform color target 70 (for example, white, gray or the like). The reference spectrum ref(λ) may be one line of data or line data obtained by averaging multiple line data. The shape of target 70 may be a half target, as shown in FIG. 7, so that reflection of illumination light of wavelengths used for imaging and diffracted in imaging order (m) be reflected by the target 70 is possible, while reflection of light of the wavelengths but diffracted in a lower order (m') may not be possible.

Figure 7:
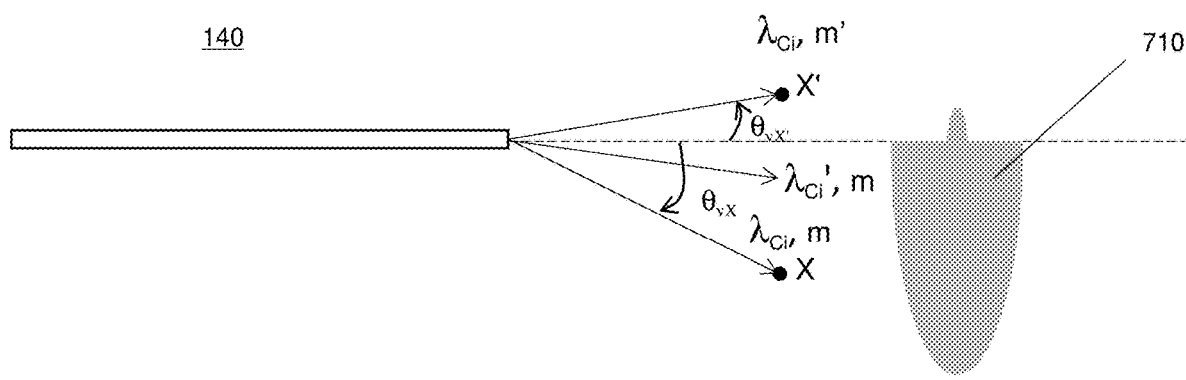
FIG. 7 illustrates illumination and diffraction of half target according to an exemplary aspect of the present disclosure.
Figure 8:
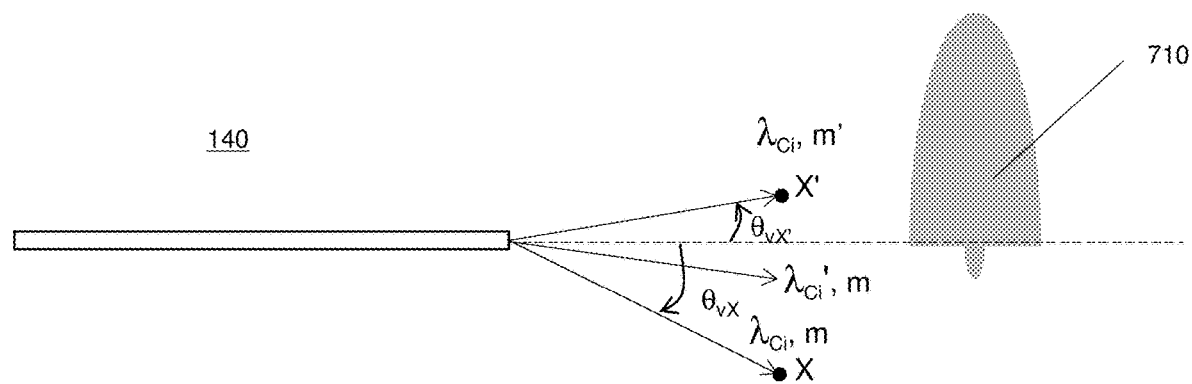
FIG. 8 illustrates illumination and diffraction of the half target of FIG. 7 rotated by 180 degrees.

The ghost/imaging ratio α(λ) may be a ratio between line data of a SEE image obtained with a half target as shown in FIG. 7 (imaging), and line data of a SEE image obtained with the same target but rotated by 180 degrees (ghost) as shown in FIG. 8, where reflection of illumination light of wavelengths used for imaging and diffracted in an imaging order (m) may not be possible, while reflection of light of wavelengths diffracted in a lower order (m') may be possible, for example, at least at a low view angle. Instead of rotating the target by 180 degrees, the probe 120 can be rotated.

Figure 9:
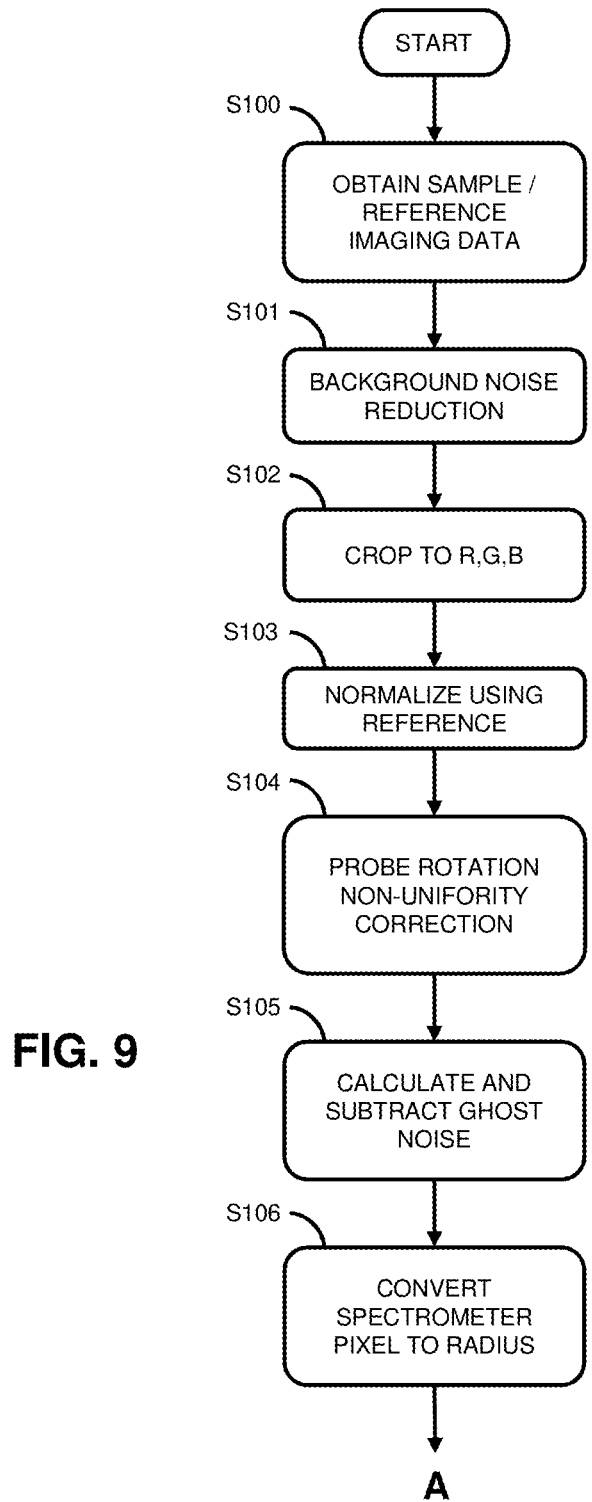
FIGS. 9 and 10 illustrate a flow chart according to according to an exemplary aspect of the present disclosure.
Figure 10:
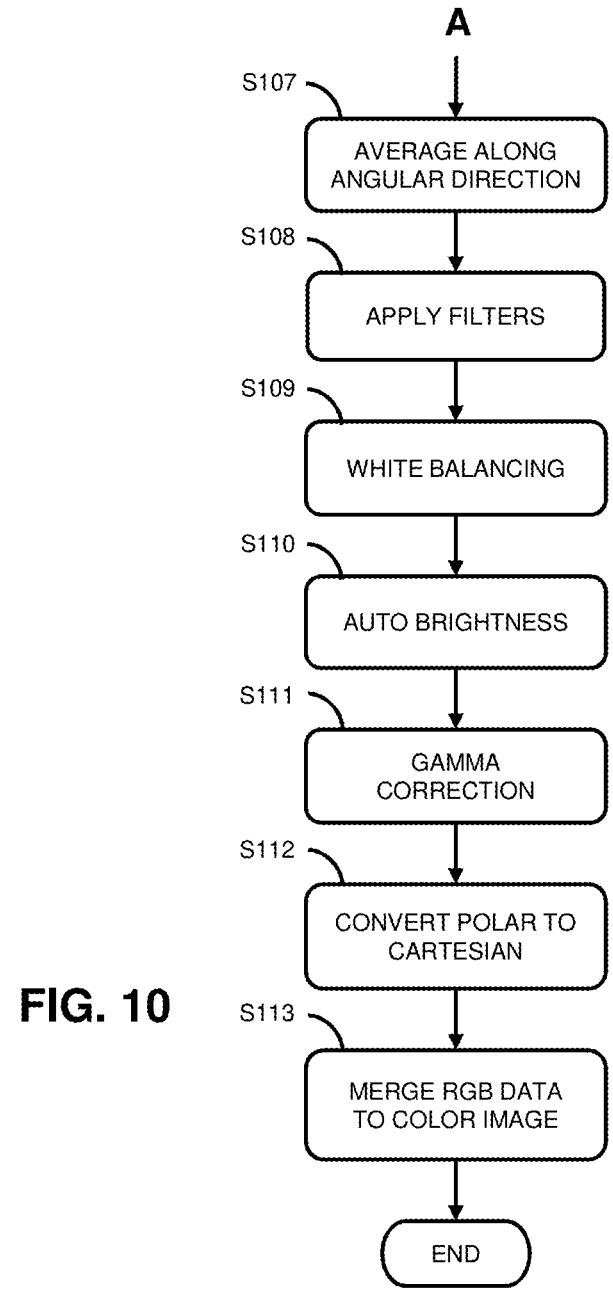

FIGS. 9 and 10 illustrate a process according to one or more aspects of the present disclosure.

Samples or reference imaging data are obtained or retrieved in step S100. Background noise reduction takes place in step S101. The data is cropped to RGB (red, green, blue) in step S102 and is then normalized using a reference in step S103. Probe rotation non-uniformity correction occurs in step S104. Ghost noise is calculated and subtracted in step S105. Spectrometer pixels are converted to radius in step S106 and an average is made along an angular direction in step S107. Filters are applied in step S108 and white balancing occurs in step S109. Auto brightness and gamma correction takes place in steps S110 and S111. Polar results are converted to Cartesian coordinates in S112 and the RGB data is merged to a color image in S114.

FIGS. 9 and 10 may represent image reconstruction in a color-forwarding SEE apparatus. The ghost reduction process may be applied. After normalization using a reference spectrum. The ghost reduction process may be applied after correction of distortion due to probe rotation non-uniformity. The ghost reduction process may be applied before coordinate conversion such as spectrometer-pixel to radius in polar coordination, or polar to Cartesian.

According to other aspects of the present disclosure, α(λ) may be replaced with a smaller value to avoid over-compensation of ghost noise. For example, α(λ) may be replaced with α(λ)/2. The ghost reduction process may also be applied to a wavelength λ in a state where a corresponding wavelength in the reduction process is smaller than λ, λ<λ'. The ghost reduction process may also be applied for view angles where $-\theta_v' < \theta_v$.

The ghost or signal ratio of the SEE apparatus may be obtained prior to imaging. A reference spectrum may be obtained by a non-uniform shape target, for example a half circle or the like. A subtraction process may be applied to a partial spectral range for imaging. A ghost image may be subtracted partially to avoid over-compensation. Color SEE may be configured using three different diffraction orders.

As described above, an image processing apparatus according to one or more aspects of the present disclosure may include at least one memory and at least one processor that executes instructions stored in the memory to receive an input image based on image data, output noise-reduced output data based on a result of the processing noise reduction processing, execute noise reduction processing on the image data, and output noise-reduced output data based on a result of the noise reduction processing, wherein the noise reduction processing calculates a value using reference pixels based on a first frequency range, and subtracts a value using pixels based on a second frequency range.

As described above, an image processing method according to one or more aspects of the present disclosure may include receiving an input image based on image data, executing noise reduction processing on the image data, and outputting noise-reduced output data based on a result of the noise reduction processing, wherein the noise reduction processing calculates a value using reference pixels based on a first frequency range, and subtracting a value using pixels based on a second frequency range.

Additional features or aspects of present disclosure can also advantageously implement one or more AI (artificial intelligence) or machine learning algorithms, processes, techniques, or the like, to execute SEE ghost noise reduction processing on the image data. Such AI techniques use a neural network, a random forest algorithm, a cognitive computing system, a rules-based engine, or the like, and are trained based on a set of data to assess types of data and generate output. For example, a training algorithm can be configured to execute SEE ghost noise reduction processing on the image data. The model(s) can be configured as software that takes images as input and returns predictions for the given images as output. The model(s) can be an instance of a model architecture (set of parameter values) that has been obtained by model training and selection using a machine learning and/or optimization algorithm/process. A model can generally include, for example, an architecture defined by a source code (e.g. a convolutional neural network including layers of parameterized convolutional kernels and activation functions, or the like) and configuration values (parameters, weights, features, or the like) that are initially set to random values and are then over the course of the training iteratively optimized given data example, an objective function (loss function), an optimization algorithm (optimizer), or the like.

At least some of the medical images of detailed positional configurations of the patient anatomy relative to the catheter position can be used as input data and provided to the training algorithm. Initial images, output values and detailed positional configurations of the catheter position relative to the patient anatomy can be stored in a database to execute SEE ghost noise reduction processing on the image data for new data. Through visualization guidance of device-to-image registration that are generated using input mapping to the model(s) or through expert research, machine learning can find parameters for AI processes. The training algorithm is configured to learn physical relationships in the input data to best describe these relationships or correlations. The data sets include information based on a number of factors including, for example, the acquired images, the number of acquired images, the angle of the image, the position of the image, detailed positional configurations of the medical device relative to the branching model, or the like. The data is evaluated using a weighted evaluation where the weights are learned through a training process, through subject matter specifications, or the like. Deep learning mechanisms can augment an AI process to identify indicators in the image data that can include, for example, new data images, output values or positional configurations of the catheter position relative to the patient anatomy, or the like.

Various modifications and alterations based on the present disclosure may become apparent to those skilled in the art, and the features of the present disclosure may be applied to any type of system including OCT, IVUS, or the like.

OTHER EMBODIMENTS

Embodiment(s) of the present disclosure can also be realized by a computerized configuration(s) of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computerized configuration(s) of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computerized configuration(s) may comprise one or more processors, one or more memories, circuitry, or a combination thereof (e.g., central processing unit (CPU), micro processing unit (MPU), or the like), and may include a network of separate computers or separate processors to read out and execute the computer executable instructions. The computer executable instructions may be provided to the computerized configuration(s), for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. An image processing apparatus comprising:
    a probe with an illumination fiber and a detection fiber, the illumination fiber being configured for optical communication with a light source; and
    a controller comprising:
        at least one memory; and
        at least one processor that executes instructions stored in the memory to:
        receive an input image based on image data;
        execute noise reduction processing on the image data by using view angle and rotation angle data of the probe to calculate a value using reference pixels based on a first frequency range, and subtract a second value using pixels based on a second frequency range; and
        output noise-reduced image data based on a result of the noise reduction processing,
    wherein ghost noise is reduced in the image reconstruction process.

2. The image processing apparatus according to claim 1, wherein the noise reduction processing comprises one or more of:
    obtaining sample or reference imaging data;
    background/noise reduction on the image data;
    normalizing using a reference; and
    averaging along an angular direction.

3. The image processing apparatus according to claim 1, wherein the noise reduction processing comprises calculating and subtracting ghost noise.

4. The image processing apparatus according to claim 1, wherein the noise reduction processing comprises one or more of:
    applying filters;
    white balancing;
    auto brightness; and
    gamma correction.

5. The image processing apparatus according to claim 1, further comprising:
    a spectrometer configured to measure light reflected from a sample that has been illuminated by the light source,
    wherein the noise reduction processing comprises:
    converting a spectrometer pixel to a radius, or
    polar to Cartesian conversion.

6. The image processing apparatus according to claim 1, wherein the noise reduction processing comprises one or both of:
    merging RGB (red, blue, green) data to a color image; and
    cropping the image data to red, green, or blue.

7. The image processing apparatus according to claim 1, wherein the at least one processor further executes instructions to perform artificial intelligence or machine learning.

8. The image processing apparatus according to claim 7, wherein the artificial intelligence or machine learning is iterative.

9. An image processing method for an image processing apparatus comprising a probe with an illumination fiber and a detection fiber, and a controller with at least one memory and at least one processor, the illumination fiber being configured for optical communication with a light source, the image processing method comprising:
    causing the controller to execute instructions to implement steps comprising:
    receiving an input image based on image data;

executing noise reduction processing on the image data by using view angle and rotation angle data of the probe to calculate a value using reference pixels based on a first frequency range, and subtract a second value using pixels based on a second frequency range; and output noise-reduced image data based on a result of the noise reduction processing, wherein ghost noise is reduced in the image reconstruction process.

10. The image processing method according to claim 9, wherein the noise reduction processing comprises one or more of:
    obtaining sample or reference imaging data;
    background/noise reduction on the image data;
    normalizing using a reference; and
    averaging along an angular direction.

11. The image processing method according to claim 9, wherein the noise reduction processing comprises calculating and subtracting ghost noise.

12. The image processing method according to claim 9, wherein the noise reduction processing comprises one or more of:
    applying filters;
    white balancing;
    auto brightness; and
    gamma correction.

13. The image processing method according to claim 9, wherein the image processing apparatus further comprises:
    a spectrometer configured to measure light reflected from a sample that has been illuminated by the light source,
    wherein the noise reduction processing comprises:
    converting a spectrometer pixel to a radius, or
    polar to Cartesian conversion.

14. The image processing method according to claim 9, wherein the noise reduction processing comprises one or both of:
    merging RGB (red, blue, green) data to a color image; and
    cropping the image data to red, green, or blue.

15. The image processing method according to claim 9, further comprising performing artificial intelligence or machine learning.

16. The image processing method according to claim 15, wherein the artificial intelligence or machine learning is iterative.

17. A non-transitory storage medium storing a program for causing a computer to execute an image processing method for an image processing apparatus comprising an illumination fiber, a detection fiber, and a controller with at least one memory and at least one processor, the illumination fiber being configured for optical communication with a light source, the at least one processor executing instructions stored in the memory to implement the image processing method comprising:
    receiving an input image based on image data;
    executing noise reduction processing on the image data by using view angle and rotation angle data of the probe to calculate a value using reference pixels based on a first frequency range, and subtract a second value using pixels based on a second frequency range; and
    output noise-reduced image data based on a result of the noise reduction processing,
    wherein ghost noise is reduced in the image reconstruction process.

* * * * *